United States Patent [19]

Onopchenko et al.

[11] 4,016,206
[45] Apr. 5, 1977

[54] PROCESS FOR PREPARING PYROMELLITIC ACID

[75] Inventors: Anatoli Onopchenko, Monroeville; Johann G. D. Schulz, Pittsburgh, both of Pa.

[73] Assignee: Gulf Research & Development Company, Pittsburgh, Pa.

[22] Filed: Dec. 18, 1972

[21] Appl. No.: 316,422

[52] U.S. Cl. .......................................... 260/524 N
[51] Int. Cl. ........................................... C07c 63/32
[58] Field of Search ............................... 260/524 N

[56] References Cited

| | | |
|---|---|---|
| 2,245,528 | 6/1941 | Loder .......................... 260/524R |
| 3,532,746 | 10/1970 | Ember ......................... 260/524R |

FOREIGN PATENTS OR APPLICATIONS 907,926  10/1962  United Kingdom .......... 260/524 X

OTHER REFERENCES

Akhmetov: Sci. Res. Inst. Petrochem. Mfg. Ufa, Neftekhimiya, 10, No. 6, pp. 879–882. (1970).
Sittig: Hydrocarbon Processing & Petroleum Refiner, July 1962, Vol. 41, No. 7, pp. 119–125.

*Primary Examiner*—Lorraine A. Weinberger
*Assistant Examiner*—Richard D. Kelly
*Attorney, Agent, or Firm*—Meyer Neishloss

[57] ABSTRACT

An improvement in the process wherein durene is subjected to liquid phase oxidation with aqueous nitric acid to obtain pyromellitic acid which involves subjecting durene to pretreatment with oxygen in the presence of a cobalt compound dissolved in a lower carboxylic acid.

9 Claims, No Drawings

PROCESS FOR PREPARING PYROMELLITIC ACID

This invention relates to an improvement in the process wherein durene is subjected to liquid phase oxidation with aqueous nitric acid to produce pyromellitic acid.

When durene is subjected to liquid phase oxidation with aqueous nitric acid, high temperatures of at least about 200° C. are required to obtain conversion thereof to pyromellitic acid. Unfortunately, as pointed out in Brownstein's Closet in Chemical Technology, 69, February 1971, page 69, such process results in a low yield of pyromellitic dianhydride and/or its precursor pyromellitic acid of less than 25 per cent. We believe that at the high temperatures employed, a substantial breakdown of durene occurs to form $CO_2$ and water. Bartolome et al. in U.S. Pat. No. 3,165,548 have converted durene to pyromellitic acid, but the procedure is complicated and requires premixing the compound to be oxidized with nitric acid below oxidation temperature, leading the resultant mixture with turbulent flow in the form of a turbulent jet into the lower end of a vertically elongated reaction zone filled with reaction liquid and maintained adiabatically under oxidation temperature and pressure, the velocity of flow of the mixture decreasing to at least one-third upon entry into the reaction zone so as to form a vortex with hot reaction product being sucked back to the point of entry of the mixture while avoiding a gas space at the upper end of the reaction zone and withdrawing reaction product at the upper end of the reaction zone. Lederle et al., in U.S. Pat. No. 2,892,868, oxidize durene with oxygen in the presence of a cobalt-containing catalyst at temperatures of about 300° to 400° F. (about 149° to 204° C.) to obtain durylic acid. A. G. Akhmetov et al. in Sci. Res. Inst. Petrochem Mfg., Ufa, *Neftekhimiya*, 10, No. 6, pages 879 to 882 (November-December 1970) allegedly obtain pyromellitic acid by first treating durene with oxygen in the presence of a cobalt salt, but in the absence of a solvent, at high temperatures of 165° to 170° C. and then subject the durylic acid obtained to oxidation with nitric acid.

We have found that in the process wherein durene is subjected to liquid phase oxidation with aqueous nitric acid under conditions wherein durene is normally converted in low yields to pyromellitic acid and where large amounts of degradation products, such as $CO_2$ and water, are normally formed, increased yields of pyromellitic acid are obtained if durene is first subjected to oxidation with molecular oxygen in the presence of a cobalt compound soluble in a lower carboxylic acid solvent under conditions such that durene is substantially converted to a corresponding diacid thereof and small amounts of durylic acid and triacid are formed.

We have found that placing two carboxyl groups on the benzene molecule confers stabilization so that when the resulting diacid is further subjected to nitric acid oxidation at high temperatures, the aromatic structure is not subject to appreciable degradation and substantially all of the remaining methyl groups on the benzene ring are converted to carboxyl groups. It is apparent that the procedure herein will greatly reduce the amount of nitric acid required for oxidation. And, since durene is a relatively costly chemical, the conversion thereof to the desired pyromellitic acid, rather than to undesired $CO_2$ and water, renders the instant process commercially attractive.

The components required in the pretreatment stage are the following: durene, a gas containing molecular oxygen, a lower carboxylic acid and a cobalt compound soluble in the reaction mixture.

In the pretreatment stage, any gas containing molecular oxygen, such as oxygen itself or air, can be used. The amount of oxygen used is at least the amount stoichiometrically required to convert at least two of the methyl substituents on the durene molecule to carboxyl groups. Since complete utilization of oxygen may not occur in all cases, it is preferable to use amounts in excess of those amounts stoichiometrically required, for example, from about two to about 20 molar excess.

In order to convert at least two of the methyl substituents on the durene molecule during the pretreatment stage, and to effect such conversion at relatively low temperatures, it is imperative that a lower carboxylic acid having from two to four carbon atoms, such as acetic acid, propionic acid and normal butyric acid, be used. The amount of lower carboxylic acid used can vary over a wide range, as long as a substantially homogeneous liquid phase is present during the pretreatment step. Thus, the weight ratio of lower carboxylic acid to durene can be from about 1:10 to about 10:1, preferably from about 1:5 to about 5:1.

Cobalt can be used in the form of any compound, preferably, as a salt, soluble in the reaction mixture. Thus, the cobalt compound can be inorganic or organic, for example, a cobaltous or cobaltic sulfate, nitrate, acetate, propionate, butyrate, isovalerate, benzoate, toluate, naphthenate, salicylate, acetyl acetonate, etc. Of these we prefer to employ cobaltous or cobaltic acetate. The amount of cobalt compound employed can vary over a wide range corresponding, for example, to at least about 0.3 and as high as about 10, or even higher, per cent by weight of cobalt metal, based on the lower carboxylic acid, although we prefer to use from about 0.5 to about five per cent by weight of cobalt.

Although the pretreatment stage can proceed without a promotor, in some cases in order to reduce the induction period, about 0.1 to about 10 per cent by weight, preferably from about 1 to about 5 per cent by weight, of a conventional promotor, such as an aldehyde, ketone, peroxide or any compound capable of furnishing free radicals under the reaction conditions employed in the pretreatment can be used. Specific examples of these are acetaldehyde, methyl ethyl ketone, benzoyl peroxide, t-butylhydroperoxide, ozone, etc.

Water of reaction need not be removed from the reaction mixture during the pretreatment stage.

We have found, surprisingly, that relatively mild temperatures are satisfactory in the pretreatment stage in order to convert at least two of the methyl substituents in the durene molecule to carboxyl groups. Thus, the temperature can be as low as about 80° C. and as high as about 140° C. Preferably, however, the temperature is maintained in the range of about 100° to about 120° C. As long as the reaction mixture is maintained in a substantially liquid phase any pressure can be employed. A pressure of about atmospheric to about 1000 pounds per square inch gauge, or even higher, preferably from about 100 to about 400 pounds per square inch gauge, is sufficient. The reaction period is from about 10 minutes to about 20 hours, preferably from about 1 to about 5 hours.

At the end of the pretreatment stage the intermediate reaction products of durene can be recovered in any suitable manner. For example, after the reactor contents have been cooled and then depressed, an equal volume of water is added thereto, resulting in the precipitation of the intermediate oxidation products of durene, which are filtered. The solids are then washed with water to remove residual lower carboxylic acid and cobalt catalyst. The solids so obtained are then subjected to oxidation with nitric acid to obtain the desired pyromellitic acid. The filtrate from the pretreatment stage can be concentrated to remove water of reaction therefrom, leaving behind most of the lower carboxylic acid and cobalt, which can then be reused in another pretreatment step. If desired, the crude product from the pretreatment stage can be evaporated to dryness to remove therefrom water of reaction and the lower carboxylic acid. The remaining solids, constituting the partially oxidized products of durene and cobalt compound used, can then be subjected to reaction with nitric acid.

The nitric acid reaction of the partially oxidized products of durene can be effected with aqueous nitric acid whose initial concentration is from about 5 to about 70 per cent, preferably from about 20 to about 40 per cent. The amount of nitric acid employed, determined as the molar ratio of 100 per cent nitric acid relative to the partially oxidized products of durene is from about 2:1 to about 18:1, preferably in the range of about 4:1 to about 12:1. The reaction temperature can be as low as about 155° C. or as high as about 200° C., or even higher, but preferably will be in the range of about 165° to about 190° C. Below about 155° C. the partially oxidized durene is not susceptible to any appreciable further oxidation, while at very high temperatures much beyond 200° C. excessive amounts of degradation products are obtained. The pressure need only be high enough to maintain the desired reaction temperature, that is, from about atmospheric to about 1000 pounds per square inch gauge, or even higher, preferably from about 200 to about 500 pounds per square inch gauge. The reaction time can be from about 0.1 to about 10 hours, preferably from about 1 to about 5 hours.

At the end of the reaction period the desired pyromellitic acid is recovered from the reaction product. Thus, the reactor can be cooled and depressured and the contents thereof concentrated by evaporation at 100° C. under reduced pressure. The resultant product is cooled to room temperature and pyromellitic acid crystallizes out of solution. The crystalline material is recovered by filtration, washed with water to remove residual nitric acid therefrom and then dried in an oven to remove moisture. The remaining solids constitute the desired pyromellitic acid.

The process can be further illustrated by the following:

EXAMPLE I

Into a 1-liter, 316-stainless steel autoclave, equipped with a magnetic stirrer, a heating mantel and a temperature controlling device, there was introduced 20 grams of cobaltous acetate tetrahydrate, 460 grams of acetic acid, and 60 grams of durene. The autocalve was brought up to operating conditions of 105° C. and 300 pounds per square inch gauge of oxygen pressure. The reaction mixture was maintained at the defined temperature and pressure for a period of 15 hours, after which the autocalve was cooled, depressured, and crude product mixture withdrawn therefrom. The crude product mixture was diluted with approximately equal volume of cold water, and filtered to separate solids therefrom. The filtrate was evaporated to dryness on a rotary evaporator, and additional solids were recovered from the residue by extraction with acetone. The combined solids were washed with hydrochloric acid to remove any cobalt catalyst still in the product, followed by two washings with water. On drying the product in a vacuum oven, a total of 75 grams of solid acids were obtained. Analysis of the mixture by vapor phase chromatography indicated that 65 grams of dicarboxylic acids (75 per cent efficiency) and 10 grams of monocarboxylic acid (13.6 per cent efficiency) were formed from durene. The distribution of the dicarboxylic acid portion of the product was 4,6-dimethylisophthalic acid (59 per cent), 2,5-dimethylterephthalic acid (38 per cent), and 4,5-dimethylphthalic acid (3 per cent).

EXAMPLE II

The run of Example I was repeated with 20 grams of cobaltous acetate tetrahydrate, 440 grams of acetic acid, 60 grams of durene, and 48 grams of methyl ethyl ketone at 105° C. and 300 pounds per square inch gauge of oxygen pressure over a period of 6 hours. The work-up was accomplished by evaporating the crude product mixture to dryness to afford 103.4 grams of product acids, including 20 grams of cobalt catalyst. Analysis of the organic portion of the mixture by vapor phase chromatography indicated the mixture to contain 52.3 grams of dicarboxylic acids (60.2 per cent efficiency) and 31.3 grams of tricarboxylic acid (31 per cent efficiency). The isometric distribution of the dicarboxylic acids was 4,6-dimethylisophthalic acid (59.8 per cent), 2,5-dimethylterephthalic acid (35.6 per cent), and 4,5-dimethylphthalic acid (4.6 per cent).

EXAMPLE III

The run of Example I was again repeated with 20 grams of cobaltous acetate tetrahydrate, 10 grams of methyl ethyl ketone, 452 grams of acetic acid, 60 grams of durene, and 53 grams of n-butane. The temperature during the reaction was 105° C., the pressure was 300 pounds per square inch gauge and the reaction time was 5.5 hours. On work-up as in Example II, a total of 91 grams of acids and catalyst was recovered. Analysis of the organic portion of the mixture by vapor phase chromatography indicated 62 grams of dicarboxylic acids (71.5 per cent efficiency) and 13 grams of tricarboxylic acid (13 per cent efficiency) to be present in a mixture. The isomeric distribution of the dicarboxylic acids was 4,6-dimethylisophthalic acid (62 per cent), 2,5-dimethylterephthalic acid (35 per cent), and 4,5-dimethylphthalic acid (3 per cent).

EXAMPLE IV

A total of 103.4 grams of the solid product mixture obtained in Example II was charged into the autoclave together with 300 grams of 70 per cent nitric acid (Specific Gravity of 1.42), and 200 grams of water. The contents of the reactor were subjected to a temperature of 165° C. and 200 pounds per square inch gauge for 1 hour, after which the autocalve was cooled, depressured, and the contents withdrawn therefrom. The crude product mixture was concentrated in a rotary evaporator, cooled, and filtered. After several washings with cold water, the solid product was dried in a vacuum oven overnight at 150° C. A total of 80 grams of pyromellitic acid was obtained, corresponding to an efficiency of 71 per cent based on the original durene feed. Vapor phase chromatography showed pyromellitic acid to be of high purity. Titration of the aqueous phase with standardized base, indicated that 58 per cent of the initial nitric acid was consumed in the reaction. We have found that when durene is subjected to reaction with only nitric acid as in this Example IV, about 80 per cent of the initial nitric acid was consumed, and the efficiency to pyromellitic acid was only 36.7 per cent.

EXAMPLE V

Oxidation of 91 grams of the recovered solids of Example III with 300 grams of 70 per cent nitric acid in 200 grams of water for 1 hour at 165° C. and 200 pounds per square inch gauge of pressure using the procedure of Example IV resulted in the isolation of 88 grams of pyromellitic acid. Over-all efficiency based on the initial durene was 77.8 per cent.

EXAMPLE VI

A fifty-gram sample of the product of Example I was treated with 200 grams of 70 per cent aqueous nitric acid and 150 grams of water for 2 hours at 165° C. and a pressure of 200 pounds per square inch gauge. The autoclave was cooled, depressured and the product withdrawn for evaporation to dryness in a rotary evaporator. The residue was then continuously extracted with methanol. On evaporation of methanol in a rotary evaporator, followed by drying of the product in a vacuum oven at 150° C., a total of 60 grams of pyromellitic acid was obtained having a melting point of 268° to 272° C. This corresponds to an efficiency of 79.4 per cent based on the original durene charged. Analysis by vapor phase chromatography gave only one sharp peak on the chromatogram for pyromellitic acid.

Obviously, many modifications and variations, as hereinabove set forth, can be made without departing from the spirit and scope thereof, and therefore only such limitations should be imposed as are indicated in the appended claims.

We claim:

1. In a process wherein durene is subjected to oxidation with nitric acid at a temperature of at least about 155° for about 0.1 to about 10 hours to convert said durene to pyromellitic acid, the improvement which comprises subjecting said durene to pretreatment with a gas containing molecular oxygen in a lower carboxylic acid having from two to four carbon atoms having dissolved therein a cobalt compound corresponding to about 0.1 to about 10 per cent by weight of cobalt, based on said lower carboxylic acid said cobalt being the sole catalyst employed, the weight ratio of said lower carboxylic acid to durene being from about 1:10 to about 10:1, at a temperature of about 80° to about 140° C. for about 10 minutes to about 20 hours sufficient to convert substantially all of the durene to the corresponding diacids thereof and to small amounts of durylic acid and triacid.

2. The process of claim 1 wherein said pretreatment is effected in a temperature range of about 100° to about 120° C.

3. The process of claim 1 wherein said cobalt compound is cobalt acetate.

4. The process of claim 1 wherein said lower carboxylic acid is acetic acid.

5. The process of claim 1 wherein the nitric acid has an initial concentration of about 5 to about 70 per cent.

6. The process of claim 1 wherein the nitric acid has an initial concentration of about 20 to about 40 per cent.

7. The process of claim 1 wherein said nitric acid oxidation temperature is in the range of about 165° to about 190° C.

8. The process of claim 1 wherein a promotor is also present in the pretreatment stage.

9. The process of claim 8 wherein said promotor is methyl ethyl ketone.

* * * * *